United States Patent [19]
Spiegel et al.

[11] Patent Number: 5,374,616
[45] Date of Patent: Dec. 20, 1994

[54] COMPOSITIONS CONTAINING SPHINGOSYLPHOSPHORYLCHOLINE AND THE USE THEREOF AS A CELLULAR GROWTH FACTOR

[75] Inventors: Sarah Spiegel, Potomac, Md.; Naishadh N. Desai, Washington, D.C.

[73] Assignee: Georgetown University, Washington, D.C.

[21] Appl. No.: 778,662

[22] Filed: Oct. 18, 1991

[51] Int. Cl.$^5$ .................. A61K 31/66; A61K 37/26; A61K 37/36; C12N 5/06
[52] U.S. Cl. .................. 514/4; 435/240.31; 514/12; 514/114
[58] Field of Search .................. 514/4, 114, 12; 435/240.54, 244, 240.31

[56] References Cited

U.S. PATENT DOCUMENTS 4,816.450 3/1989 Bell et al. .................. 536/5
5,110,595 5/1992 Wang .................. 514/4

FOREIGN PATENT DOCUMENTS 222491 5/1985 Germany .................. 435/240.54

OTHER PUBLICATIONS

Chemical Abstract 110:5762z (1989).
Chemical Abstract 110:229,598p (1989).
*Biochem And Biophysical Research Communication*; vol. 169, No. 2, Jun. 15, 1990, pp. 673–679, "Effects Of Various Lysosphingolipsids On Cell Growth, Morphology And Lipid Composition In Three Neuroblastoma Cell Lines," Sugiyama et al.
*Journal Of Biol. Chem.*, vol. 265, No. 1, Jan. 5, 1990, pp. 76–81 (1990), "Sphingosine Stimulates Cellular Proliferation Via A Protein Kinase C–Independent Pathway," Zhang et al.
*Journal Of Biol. Chem.*, vol. 265, No. 345, Dec. 5, 1990, pp. 21309–21316, "Increases In Phosphatidic Acid Levels Accompany Sphingosine-Stimulated Proliferation Of Quiescent Swiss 3T3 Cells," Zhang et al.
*Journal Of Cell Biol.*, vol. 114, (1991), "Sphingosine-1--Phosphate, A Novel Lipid, Involved In Cellular Proliferation," Zhang et al.

Primary Examiner—Jeffrey E. Russel
Attorney, Agent, or Firm—Oblon, Spivak, McClelland, Maier & Neustadt

[57] ABSTRACT

A pharmaceutical composition for promoting cellular proliferation in a mammal, which comprises:
 a) an amount of an active ingredient effective to promote said cellular proliferation, and
 b) a pharmaceutically acceptable carrier, said active ingredient comprising, at least, sphingosylphosphorylcholine.

3 Claims, 3 Drawing Sheets

COMPOSITIONS CONTAINING SPHINGOSYLPHOSPHORYLCHOLINE AND THE USE THEREOF AS A CELLULAR GROWTH FACTOR

The work leading to the present invention was supported by Research Grant 1R01 GM 43880 from the National Institutes of Health, and the U.S. Government may, therefore, have rights arising from the same.

BACKGROUND OF THE INVENTION

1. Field of the Invention

The present invention relates to compositions containing sphingosylphosphorylcholine and the use thereof as a cellular growth factor.

2. Description of the Background

The biochemical mechanisms whereby eukaryotic cells regulate their proliferation are not well understood. However, an attempt has been made to approach this problem by identifying the second messengers responsible for initiating the progression of $G_o$-arrested cells into the S phase. In Swiss 3T3 cells, which are sensitive to a wide variety of mitogenic agents, some growth factors appear to function through conventional second messengers such as cAMP, whereas others use the signal pathways associated with increased degradation of polyphosphoinositides leading to the generation of lipid second messengers. Diacylglycerol (DAG) is an endogenous activator of protein kinase C and inositol triphosphate (IP$_3$) causes a release of Ca$^{+2}$ from intracellular stores. Although the roles of these intracellular second messengers have been well characterized, not all of the second messenger systems involved in cell growth regulation have been elucidated. In particular, it is clear that the early responses of quiescent cells to a variety of growth factors, such as changes in Ca$^{+2}$ and pH$_i$, and activation of phospholipase C and protein kinase C, are insufficient by themselves to cause the cells to initiate DNA synthesis. Thus, there are clearly some undiscovered intracellular second-messenger pathways which are important for cell growth regulation.

The present inventors recently discovered that sphingosine at low concentrations stimulates cell proliferation of quiescent 3T3 fibroblasts via a protein kinase C-independent pathway. See Spiegel, S. et al, *J. Biol. Chem.* 265, 76–81 (1990). The present inventors have also recently demonstrated that the mitogenic effect of sphingosine is mediated by a rapid rise in the levels of phosphatidic acid and of sphingosine-1-phosphate which are both potent mitogens for 3T3 cells. See Spiegel, S., *J. Biol. Chem.* 265, 21309–21316 (1990) and Spiegel, S. et al, *J. Cell Biol.* 114, 155–167 (1991).

However, a need exists for mitogenic compounds of increased potency which have little or no loss of cell viability associated therewith.

SUMMARY OF THE INVENTION

Accordingly, it is an object of the present invention to provide a pharmaceutical composition having remarkably potent mitogenic activity for a wide variety of cell lines.

It is also an object of the present invention to provide a pharmaceutical composition which causes little or no loss of cell viability.

Further, it is also an object of the present invention to provide a method for promoting cellular proliferation in a mammal.

Accordingly, these objects and others are provided by a pharmaceutical composition for promoting cellular proliferation in a mammal, which entails an amount of an active ingredient effective to promote said cellular proliferation; and a pharmaceutically acceptable carrier, said active ingredient including at least sphingosylphosphorylcholine.

DETAILED DESCRIPTION OF THE PREFERRED EMBODIMENTS

Figure 1:
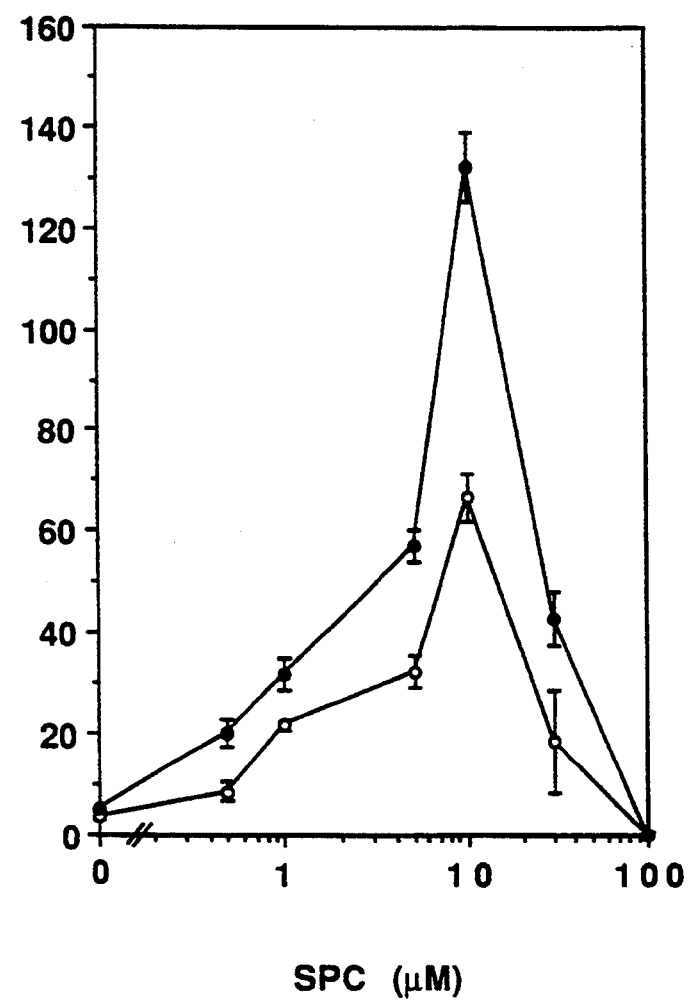
FIG. 1 illustrates a dose response for the stimulation of DNA synthesis in Swiss 3T3 cells by sphingosylphosphorylcholine (SPC).

In accordance with the present invention, it has been surprisingly discovered that sphingosylphosphorylcholine and pharmaceutical compositions containing the same exhibit a remarkably potent mitogenic effect for a wide variety of cell lines. Quite surprisingly, it has been discovered that sphingosylphosphorylcholine is a much more potent cellular growth factor than other known growth factors, including sphingosine and sphingosine-1-phosphate, and also acts synergistically with other agents such as insulin, epidermal growth factor (EGF), fibroblast growth factor (FGF) and the tumor promoter, 12-O-tetradecanoylphorbol-13-acetate (TPA), to induce cellular proliferation in mammalian cells.

The present inventors have also observed that treatment of cells with sphingosylphosphorylcholine is accompanied by pronounced morphological alterations. The use of sphingosylphosphorylcholine at low concentrations also is observed to greatly stimulate DNA synthesis and cell division. However, it has been found that sphingosylphosphorylcholine is less effective in stimulating DNA synthesis in rapidly growing normal and transformed cells.

In accordance with the present invention, sphingosylphosphorylcholine or pharmaceutical compositions containing the same are administered to a mammal in vivo or to one or more cell line cultures in vitro at low concentration. Generally, a mitogenic effect can be obtained at a concentration of sphingosylphosphorylcholine of as low as 0.1 $\mu$M. However, concentrations of about 1 $\mu$M to up to, but not including, 25 $\mu$M may be used. However, it is particularly preferred if the concentration of sphingosylphosphorylcholine used is about 10 to 20 $\mu$M. Quite surprisingly, even at the preferred concentration of about 10 to 20 $\mu$M, little or no loss of cell viability occurs. Typically, more than 95% of cells subjected to sphingosylphosphorylchlorine remain viable.

However, at high concentrations of sphingosylphosphorylcholine, such as in excess of about 100 $\mu$M, cells tested in vitro lose viability, becoming detached from plates.

Furthermore, in accordance with the present invention it has been found that sphingosylphosphorylcholine administered alone at the preferred concentration is surprisingly more mitogenic than insulin, EGF and even TPA, which is an exceptionally potent growth stimulator for Swiss 3T3 cells. Similar to the synergistic effect between insulin and other growth factors, the mitogenic response to SPC is also potentiated by insulin, EGF or FGF, for example. This surprising synergistic interaction between sphingosylphosphorylcholine and other growth factors is observed even in combination with two growth factors, such as EGF plus insulin or TPA plus insulin. While any two growth factors synergize with each other, addition of SPC causes a further potentiation of [$^3$H]thymidine incorporation.

In accordance with the present invention either sphingosylphosphorylcholine or pharmaceutical compositions containing the same or also containing other known growth factors may be administered to poultry or mammals to effect cellular proliferation. While any mammal, such as a horse, cow, pig, chicken, cat, dog or mouse, for example, may be treated, it is preferred that the mammal treated be a human. As far as poultry is concerned, any type may be treated in accordance with the present invention. However, it is preferred that chickens or ducks be treated.

The pharmaceutical composition according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonire; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain pacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the abovementioned diluents.

The diluents to be used in pharmaceutical compositions adapted to be formed into suppositories can, for example, be the usual water-soluble diluents, such as polyethylene glycols and fats (e.g. cocoa oil and high esters (e.g. C14-alcohol with C16-fatty acid)) or mixtures of these diluents.

The pharmaceutical compositions which are solutions and emulsions can, for example, contain the customary diluents, such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl) alcohols, polyoxyethylene sorbite and sorbitane esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions, such as, for example, oil and eucalyptus oil, and sweetening agents, such as, for example, saccharin).

The pharmaceutical composition according to the invention generally contains from about 0.1% to 99% of the active ingredient by weight of the total composition. However, it is generally preferred that the composition contain from about 1% to 90% the active ingredient by weight of the total composition. As noted above, the "active ingredient" may be sphingosylphosphorylcholine by itself or may be a mixture of sphingosylphosphorylcholine with one or more of insulin, EGF, FGF, sphingosine or sphingosine-1-phosphate, for example.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

Further, if desired the compositions of the present invention may be coated.

The coating materials used for coating the present composition require no further discussion. Water-permeable coating compositions are well known in the art of tablet coating. They are used in the same fashion as in coating tablets but are applied to the granules of the present composition but not to a tablet. The amount of coating composition to be applied is well defined by the above limitation: not more than about 4% of the active ingredient or ingredients must leach out into artificial saliva within a period of two minutes at 20–40° C. Among the most popular coating materials are: hydroxypropylcellulose, methylhydroxypropylcellulose, polyethylene oxide and polyvinyl pyrrolidone. These water-soluble polymers can be used alone or in admixture with water-insoluble polymers, such as ethylcellulose, polyvinylacetate, methylacrylate/methyl methacrylate, cellulose acetate propionate, cellulose acetate butyrate, cellulose acetate propionate, polyvinylidene chloride, zein, and certain waxes as long as the resulting film is water permeable. In the preferred embodiment, the coating material is applied to the present composition to the extent of at least 15% by weight of the complex. This insures almost complete taste masking. Where coating is done with water-soluble, film-formers, there is no substantial change of active ingredient availability experienced in the gastro-in-testinal juices between coated and uncoated composition particles.

Having describe the present invention, reference will now be made to certain Examples which are provided solely for purposes of illustration and are not intended to be limitative.

MATERIALS AND METHODS

Materials

[methyl³H]Thymidine (55 Ci/mmol) was purchased from Amersham. Epidermal growth factor (EGF), insulin, fibroblast growth factor (FGF) and transferrin were obtained from Collaborative Research. TPA and SPC (free base) were from Sigma Chemical Co.

Cell Culture

Swiss 3T3 (CCL 92), NIH 3T3 (CRL 1658), Moloney MSV 3T3 transformed (CRL 1568), BALB/c (TIB 80), preadipocyte or 3T3 L1 (CCL 92.1), human astrocytoma (CRL 1718), were from the American Type Culture Collection. NIH 3T3 cells transformed with a plasmid bearing the gene for FGF were from Dr. F. Kern, Lombardi Cancer Center. C6-2B cells were obtained from Dr. G. Brooker. Stock cultures of cells were routinely maintained as previously described. See Spiegel, S. et al, *Proc. Natl. Acad. Sci. USA* 84, 141–147 (1987). To obtain quiescent cultures, the cells were subcultured at a density of $1.5 \times 10^4$ cells/cm² in DMEM (JRH Biomedicals) supplemented with 2 mM glutamine, 1 mM pyruvate, penicillin (100 units/ml), streptomycin (100 μg/ml) and 10% calf serum (Colorado Serum Co.). The cells were used 7 days later when they were confluent and quiescent. See Spiegel, S. et al, *Exp. Cell Res.* 177, 414–427 (1988). Rapidly growing cells were subcultured at a density of $2.0 \times 10^3$ cells/cm² and used 3 days later. Transformed cell lines were subcultured at a density of $1.5 \times 10^3$ cells/cm² and used two days later.

Assay of DNA Synthesis

Cultures were washed with DEMEM to remove residual serum and 1 ml of DMEM supplemented with 20 μg/ml BSA and 5 μg/ml transferrin were added. The cells were treated with various growth factors or SPC and were pulsed after 18 hours with 1.0 μCi of [³H]thymidine for 6 hours. The [³H]thymidine incorporation into trichloroacetic acid-insoluble material was measured as described previously. Values are the means of triplicate determinations. Standard errors were routinely less than 10% of the mean.

Measurement of Cell Number

Cells were cultured and treated with mitogens as described above and after two days the wells were washed with DMEM to get rid of dead and floating cells. The viable cells were removed from the dishes by trypsinization and counted (Coulter Model ZBI). Data represent the mean ±SD of three independent cultures.

EXAMPLE 1

Confluent and quiescent Swiss 3T3 fibroblasts were exposed to the indicated mitogens in the absence (−) or presence (+) of SPC [³H]thymidine incorporation was measured as described above.

Each value is the mean ±SD of triplicate determinations from a representative experiment. Similar results were obtained in 10 additional experiments. The concentrations of the mitogenic agents used were as follows: SPC, 10 82 M; Insulin, 2 μg/ml; TPA, 100 nM; EGF, 10 ng/ml; FGF, 25 ng/ml. The results obtained are shown below in Table 1.

TABLE 1
EFFECTS OF SPC ON DNA SYNTHESIS IN QUIESCENT CULTURES OF SWISS 3T3 FIBROBLASTS

| Stimulant | [³H] Thymidine Incorporation (cpm × 10⁻³/well) | |
|---|---|---|
| SPC | (−) | (+) |
| None | 4.9 ± 0.5 | 93.3 ± 5.6 |
| Insulin | 12.1 ± 0.8 | 317.9 ± 23.6 |
| TPA | 50.7 ± 3.1 | 198.6 ± 6.6 |
| TPA plus Insulin | 209.9 ± 15.8 | 340.3 ± 24.2 |
| EGF | 26.2 ± 1.4 | 332.8 ± 15.6 |
| EGF | 172.7 ± 6.3 | 437.8 ± 16.1 |
| EGF plus Insulin | 19.5 ± 4 | 204.0 ± 12.1 |

From Table 1, it is observed that SPC stimulated DNA synthesis in quiescent Swiss 3T3 fibroblasts grown in a chemically defined medium as measured by [³H]thymidine incorporation. A mitogenic effect was observed at a concentration of SPC of as low as 0.1 μM and maximum stimulation of 15-fold was achieved at 10–20 μM. Up to this concentration, there was no loss of cell viability and more than 95% of the cells were viable. At high concentrations of SPC of greater than 100 μM, most of the cells became detached from the plates.

SPC alone at optimal concentrations was found to be significantly more mitogenic than insulin, EGF, and even TPA, which is an exceptionally potent growth stimulator for Swiss 3T3 cells. Similar to the synergistic effect between insulin and other growth factors, the mitogenic response to SPC was also potentiated by insulin, EGF, FGF and TPA. This synergistic interaction between SPC and growth factors was observed even in combinations with two growth factors, such as EGF plus insulin or TPA plus insulin. While any two of the growth factors synergized with each other, addition of SPC caused a further potentiation of [³H]thymidine incorporation.

Furthermore, SPC not only stimulated DNA synthesis, but also caused an increase in cell number. This may be seen in FIG. 2A. The increases in cell numbers were well correlated with the increases in DNA synthesis. This may be seen in FIGS. 1A and 2A. Further, a maximal increase in cell numbers of 100% was observed after 48 hours exposure to SPC and was comparable to the increase mediated by 10% calf serum. In contrast, other known mitogens, such as EGF, induced only a 30% increase in cell number.

Similar to other potent mitogens for these cells, SPC also induced large morphological transformations. FIG. 3 shows the morphological effects on cells treated with the tumor promoter TPA and SPC. The flattened appearance of untreated cells is contrasted with the elongated refractile appearance of cells having long projections after treatment with SPC or TPA. See FIG. 3. In SPC-treated cells, there are many loci of intense growth where the cells appear to be overgrowing. See FIG. 3D. Cells in these foci may have lost the property of contact inhibition which could cause them to detach from the surface.

Example 2

The various cell types described above were incubated in the presence of the indicated mitogens and DNA synthesis was measured as described above.

The data are expressed as [$^3$H]thymidine incorporated relative to the value obtained in the absence of added mitogens. The concentrations of the mitogens were the same as in Table 1.

TABLE 2

EFFECTS OF SPC ON DNA SYNTHESIS IN VARIOUS CELL TYPES

| Stimulant | [$^3$H] Thymidine Incorporation (fold stimulation) | | | |
|---|---|---|---|---|
| | SPC | EGF | Insulin | Insulin & SPC |
| A. Untransformed Cells | | | | |
| 1. Contact Inhibited Cells | | | | |
| Swiss 3T3 fibroblasts | 19.0 | 5.3 | 2.5 | 65.0 |
| BALB/c 3T3 fibroblasts | 4.0 | 3.9 | 3.3 | 4.8 |
| 3T3 L1 preadipocytes | 5.9 | 2.1 | 8.0 | 45.6 |
| 2. Exponentially Growing Cells | | | | |
| Swiss 3T3 fibroblasts | 3.1 | 2.0 | 3.0 | 5.5 |
| BALB/c 3T3 fibroblasts | 4.5 | 3.9 | 3.3 | 4.8 |
| NIH 3T3 fibroblasts | 3.5 | 3.0 | 2.2 | 4.8 |
| B. Transformed Cells | | | | |
| MSV 3T3 | 2.0 | 1.8 | 2.1 | 3.7 |
| Transformed 3T3 NIH | 3.7 | 1.4 | 3.0 | 6.8 |
| C6 glioma | 2.1 | ND | 0.95 | 2.3 |
| Astrocytes | 1.6 | ND | 1.8 | 2.2 |

*ND indicates no data were obtained

From the above Table, it can be seen that the mitogenic activity of SPC is not restricted to confluent and quiescent Swiss 3T3 fibroblasts. In fact, SPC stimulated DNA synthesis in other similar contact inhibited cell lines, including BALB/c, NIH 3T3 fibroblasts and preadipocytes. SPC also stimulated DNA synthesis in very divergent cell types, such as HeLa carcinoma cells, C6 rat glioma cells, transformed 3T3 cells and human astrocytes. Further, there was a corresponding increase in viable cell counts in cases examined, for which data is not shown. The mitogenic effect of SPC on rapidly dividing cells is expectedly less than on quiescent cells arrested in the $G_1$ to $F_0$ phase of the cell cycle. It is evident that rapidly growing cells respond much less to growth promoting agents since they are not locked in the $G_O$ phase. Hence, rapidly growing untransformed 3T3 fibroblasts and two transformed 3T3 fibroblasts lines behaved alike. Generally, only 2-3 fold stimulation of DNA synthesis was observed for all types of rapidly dividing cells. This is comparable to the effects of other potent mitogenic agents on transformed cell lines.

Furthermore, the present inventors have surprisingly discovered that sphingosylphosphorylcholine is a much more potent mitogenic agent than either sphingosine or sphingosine-1-phosphate. Sphingosine and sphingosine-1-phosphate are weak mitogens by themselves and require the presence of other growth factors for maximum effect. By contrast, however, sphingosylphosphorylcholine is a very potent mitogenic agent, by itself. These effects may be seen by inspection of Table 3.

EFFECT OF SPHINGOSYLPHOSPHORYLCHOLINE (SPC), SPHINGOSINE, AND SPHINGOSINE-1-PHOSPHATE (SP-1-P) ON DNA SYNTHESIS IN QUIESCENT CULTURES OF SWISS 3T3 CELLS

| Stimulants | [$^3$H] Thymidine incorporation (cpm × 10$^{-3}$/Well) | | | |
|---|---|---|---|---|
| | None | SPC | Sphingosine | SP-1-P |
| None | 4 | 93 | 7 | 37 |
| Insulin | 12 | 320 | 46 | 120 |
| EGF | 26 | 332 | 55 | 103 |

EFFECT OF SPHINGOSYLPHOSPHORYLCHOLINE (SPC), SPHINGOSINE, AND SPHINGOSINE-1-PHOSPHATE (SP-1-P) ON DNA SYNTHESIS IN QUIESCENT CULTURES OF SWISS 3T3 CELLS

| Stimulants | [$^3$H] Thymidine incorporation (cpm × 10$^{-3}$/Well) | | | |
|---|---|---|---|---|
| | None | SPC | Sphingosine | SP-1-P |
| Insulin plus EGF | 172 | 437 | 244 | 267 |

Quiescent cultures of swiss 3T3 cells were exposed to the indicated mitogens and [$^3$H]thymidine incorporation was measured. Each value is the mean of triplicate determinations from a representative experiment. Standard deviations were routinely less than 10%. Similar results were obtained in at least five additional experiments.

FIGS. 1–3 will now be explained in more detail.

FIG. 1 illustrates a dose response for the stimulation of DNA synthesis in Swiss 3T3 cells by SPC. Confluent and quiescent cultures of Swiss 3T3 cells were incubated with various concentrations of SPC in the absence (−) or in the presence (+) insulin (2 μg/ml) or TPA (100 nM) and an [$^3$H]thymidine incorporation was measured as described above. Similar results were obtained in at least five additional experiments. All concentrations of SPC above 0.1 μM were statistically significant (Student's t test), p ≦0.01 compared to the untreated cells.

FIG. 2 illustrates the stimulation of cell division by SPC.

Figure 2B:
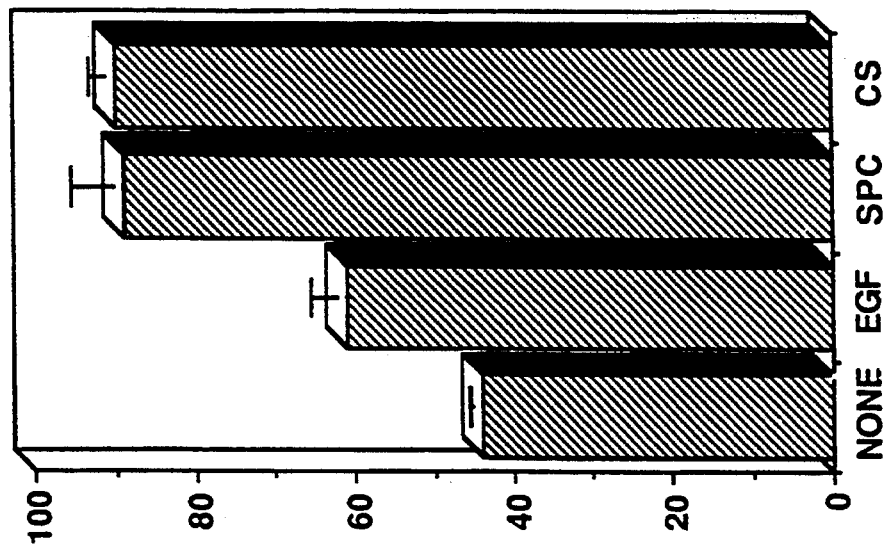
FIG. 2B illustrates the increase in cell number for various mitogens tested.
Figure 2A:
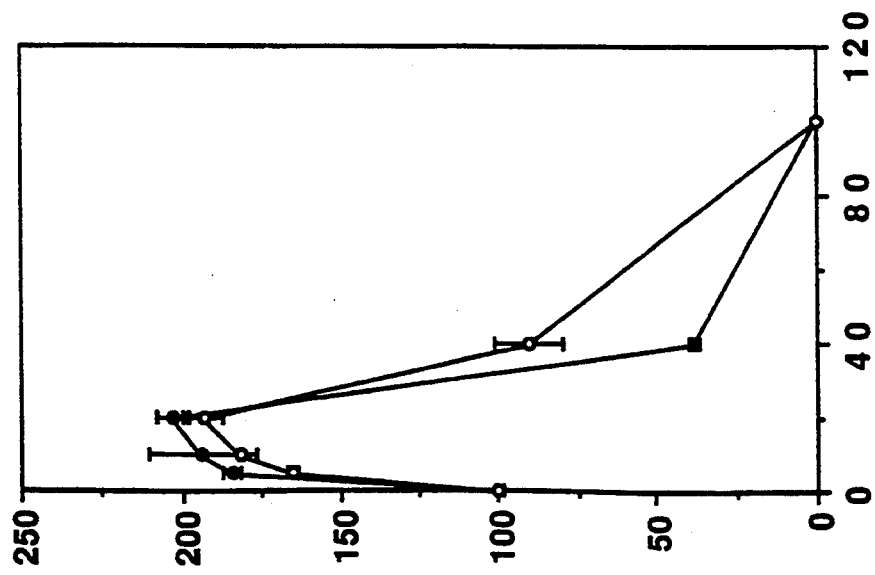
FIG. 2A illustrates the stimulation of cell division by SPC.
Figure 3A:
FIG. 3A–D illustrate morphological alterations of Swiss 3T3 cells induced by SPC or 12-o-tetradecanoylphorbol 13-acetate (TPA).
Figure 3B:
Figure 3C:
Figure 3D:

To obtain the data represented in FIG. 2A, confluent and quiescent cultures of Swiss 3T3 cells were incubated in DMEM/Waymouth (1:1) supplemented with BSA (20 μg/ml), transferrin (5 μg/ml) and treated and insulin (2 μg/ml) and treated with various concentrations of SPC in the absence (−) or in the presence (+) of insulin (2 μg/ml). After 48 hours, the cells were removed from the dishes and counted as described above. Data represent the mean ±SD of three independent cultures treated identically. The data are expressed as percent of control values obtained in the absence of added mitogens.

The data for FIG. 2B represent the increase in cell number induced by the different mitogens: SPC (20 μM); EGF (10 ng/ml) and calf serum (10%).

FIG. 3 illustrates the morphological alterations of Swiss 3T3 cells induced by SPC or TPA. In particular, confluent and quiescent cultures of Swiss 3T3 cells were incubated in DMEM/Waymount (1:1) supplemented with BSA (20 μg/ml), transferrin (5 μg/ml), in the absence (A) or in the presence of (B) 100 nM TPA or (C/D) 10 μM SPC. Photomicrographs of the cultures were taken with the aid of phase-contrast microscope 24 hours after addition of the mitogens ($\times$450). The flattened appearance of untreated cells (A) is contrasted with the elongated, refractile appearance of treated cells (B–D). (D) shows an area of overgrown cells induced by SPC.

Generally, in accordance with the present invention, concentrations of about 1 μM to up to, but not including 25 μm may be used. However, it is preferred that a concentration of SPC of about 10 to 20 μM be used. Notably, 1 μm SPC is approximately the same concentration as 1 μmol/kg or about 0.5 mg/kg. Thus, in administering SPC to poultry or mammals, about 0.5 mg to 10 mg is used per kg of body weight.

Furthermore, as noted previously, other growth factors, such as insulin, EGF and FGF may be used in conjunction with SPC. If such other factors are so used, one or more may be used in an amount of about 0.00001 mg to 0.01 mg/kg of body weight. However, more or less may be used as needed.

Thus, the present invention provides a pharmaceutical composition and a method for promoting cellular proliferation in a mammal, which contains: a) an amount of an active ingredient effective to promote the cellular proliferation, and b) a pharmaceutically acceptable carrier, the active ingredient containing, at least, sphingosylphosphorylcholine. Preferably, the pharmaceutical composition is in a form suitable for human use.

The present invention also generally provides a method of promoting proliferation of mammalian cells, which entails contacting the mammalian cells with an amount of an active ingredient effective to promote the cellular proliferation, the active ingredient containing, at least, sphingosylphosphorylcholine. Notably, this method may be either in vivo or in vitro, such that the mammalian cells having promoted proliferation are either in vivo or in vitro. Regardless of whether the method is in vivo or in vitro, this method may be practiced with any mammalian cells as defined above.

Further, where the present method is used to promote proliferation of mammalian cells in vitro, conventional culturing methods and nutrients may be used as are well known to those skilled in the art.

Having described the present invention, it will be apparent to one of ordinary skill in the art that many changes and modifications can be made to the above-described embodiments without departing from the spirit and the scope of the present invention.

What is claimed as new and desired to be secured by Letters Patent of the United States is:

1. A pharmaceutical composition for promoting cellular proliferation of mammalian cells, which comprises:
    a) an amount of active ingredient effective only to promote said proliferation of mammalian cells, and
    b) a pharmaceutically acceptable carrier, said active ingredient comprising sphingosylphosphorylcholine and at least one other growth factor selected from the group consisting of insulin, EGF, FGF, sphingosine and sphingosine-1-phosphate;
    and wherein said active ingredient comprises about 0.1 to 99% by weight of the total composition.

2. The pharmaceutical composition of claim 1, in a form suitable for human use.

3. The pharmaceutical composition of claim 1, wherein said active ingredient comprises about 1 to 90% by wt. of the total composition.

* * * * *